US006313960B2

(12) United States Patent
Marquiss et al.

(10) Patent No.: US 6,313,960 B2
(45) Date of Patent: *Nov. 6, 2001

(54) OPTICAL FILTER HOLDER ASSEMBLY

(75) Inventors: Samuel A. Marquiss, Santa Clara; Calvin D. Wong, San Carlos; Glenn R. Edwards, Palo Alto; Michael T. Taylor, Newark; Philip A. Granieri, Jr., Los Altos; Douglas N. Modlin, Palo Altos; Amer El-Hage, Menlo Park, all of CA (US)

(73) Assignee: LJL Biosystems, Inc., Sunnyvale, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/118,141

(22) Filed: Jul. 16, 1998

Related U.S. Application Data

(60) Provisional application No. 60/052,876, filed on Jul. 16, 1997, provisional application No. 60/059,639, filed on Sep. 20, 1997, provisional application No. 60/063,811, filed on Oct. 31, 1997, provisional application No. 60/072,499, filed on Jan. 26, 1998, provisional application No. 60/072,780, filed on Jan. 27, 1998, provisional application No. 60/075,414, filed on Feb. 20, 1998, provisional application No. 60/075,806, filed on Feb. 24, 1998, provisional application No. 60/082,253, filed on Apr. 17, 1998, provisional application No. 60/084,167, filed on May 4, 1998, provisional application No. 60/085,335, filed on May 13, 1998, provisional application No. 60/085,500, filed on May 14, 1998, and provisional application No. 60/089,848, filed on Jun. 19, 1998.

(51) Int. Cl.[7] .............................. G02B 5/22; G02B 7/00; F21V 17/02
(52) U.S. Cl. .................... 359/892; 359/889; 359/891; 362/324
(58) Field of Search .................... 359/892, 885, 359/894, 819, 820, 827, 830, 500, 501, 502, 889; 362/294, 322, 324; 348/743

(56) References Cited

U.S. PATENT DOCUMENTS 2,719,214   9/1955   Potter .
3,013,467   12/1961  Minsky .

(List continued on next page.)

FOREIGN PATENT DOCUMENTS 0 266 881 A1   5/1988   (EP) .
2 215 838 A    9/1989   (GB) .
2 228 081 A    8/1990   (GB) .

OTHER PUBLICATIONS

Donald G. Fink and H. Wayne Beaty, Standard Handbook for Electrical Engineers, pp. 22–2 through 22–5 (11th ed. 1978).

(List continued on next page.)

*Primary Examiner*—Audrey Chang
(74) *Attorney, Agent, or Firm*—Kolisch, Hartwell, Dickinson, McCormack & Heuser, PC

(57) ABSTRACT

Devices for using optical filters in a filter holder that enable optical filters to be simply, conveniently, and flexibly interchanged.

18 Claims, 5 Drawing Sheets

U.S. PATENT DOCUMENTS

| | | | |
|---|---|---|---|
| 3,176,577 | * 4/1965 | Frank | 359/889 |
| 3,423,581 | 1/1969 | Baer . | |
| 3,516,736 | * 6/1970 | Weaver | 359/425 |
| 3,849,654 | 11/1974 | Malvin . | |
| 3,885,162 | 5/1975 | Geertz . | |
| 3,932,023 | 1/1976 | Humer . | |
| 4,011,451 | 3/1977 | Nelson . | |
| 4,067,653 | 1/1978 | Fletcher et al. . | |
| 4,074,939 | 2/1978 | Rabl . | |
| 4,076,420 | 2/1978 | De Maeyer et al. . | |
| 4,100,416 | 7/1978 | Hirschfeld . | |
| 4,144,452 | 3/1979 | Harte . | |
| 4,150,870 | 4/1979 | d'Auria . | |
| 4,203,670 | 5/1980 | Bromberg . | |
| 4,341,957 | 7/1982 | Wieder . | |
| 4,397,560 | 8/1983 | Andresen . | |
| 4,485,430 | 11/1984 | Achiaga Fustel . | |
| 4,501,970 | 2/1985 | Nelson . | |
| 4,567,847 | 2/1986 | Linner . | |
| 4,626,684 | 12/1986 | Landa . | |
| 4,646,214 | * 2/1987 | Mendleski | 362/294 |
| 4,685,801 | 8/1987 | Minekane . | |
| 4,699,512 | 10/1987 | Koshi . | |
| 4,704,255 | 11/1987 | Jolley . | |
| 4,704,353 | 11/1987 | Humphries et al. . | |
| 4,707,067 | 11/1987 | Haberland et al. . | |
| 4,724,217 | 2/1988 | Miller . | |
| 4,730,921 | 3/1988 | Klein et al. . | |
| 4,737,464 | 4/1988 | McConnell et al. . | |
| 4,738,825 | 4/1988 | Kelln et al. . | |
| 4,741,619 | 5/1988 | Humphries . | |
| 4,753,501 | 6/1988 | Battle . | |
| 4,758,786 | 7/1988 | Hafeman . | |
| 4,762,420 | 8/1988 | Bowley . | |
| 4,772,453 | 9/1988 | Lisenbee . | |
| 4,784,275 | 11/1988 | Fridge . | |
| 4,801,804 | 1/1989 | Rosenthal . | |
| 4,802,768 | 2/1989 | Gifford et al. . | |
| 4,808,828 | 2/1989 | Kitamori et al. . | |
| 4,810,096 | 3/1989 | Russell et al. . | |
| 4,826,660 | 5/1989 | Smith et al. . | |
| 4,849,330 | 7/1989 | Humphries et al. . | |
| 4,855,930 | 8/1989 | Chao et al. . | |
| 4,868,103 | 9/1989 | Stavrianopoulos et al. . | |
| 4,873,633 | 10/1989 | Mezei et al. . | |
| 4,877,965 | 10/1989 | Dandliker et al. . | |
| 4,883,579 | 11/1989 | Humphries et al. . | |
| 4,885,087 | 12/1989 | Kopf . | |
| 4,892,409 | 1/1990 | Smith . | |
| 4,911,794 | 3/1990 | Parce et al. . | |
| 4,915,812 | 4/1990 | Parce et al. . | |
| 4,923,819 | 5/1990 | Fernandez et al. . | |
| 4,936,682 | 6/1990 | Hoyt . | |
| 4,948,442 | 8/1990 | Manns . | |
| 4,963,815 | 10/1990 | Hafeman . | |
| 4,968,148 | 11/1990 | Chow et al. . | |
| 4,979,821 | 12/1990 | Schutt et al. . | |
| 5,009,488 | * 4/1991 | Fay et al. | 359/891 |
| 5,018,866 | 5/1991 | Osten . | |
| 5,020,995 | 6/1991 | Levy . | |
| 5,039,219 | 8/1991 | James et al. . | |
| 5,047,215 | 9/1991 | Manns . | |
| 5,058,045 | 10/1991 | Ma . | |
| 5,082,628 | 1/1992 | Andreotti et al. . | |
| 5,084,246 | 1/1992 | Lyman et al. . | |
| 5,091,652 | 2/1992 | Mathies et al. . | |
| 5,095,517 | 3/1992 | Monguzzi et al. . | |
| 5,096,807 | 3/1992 | Leaback . | |
| 5,104,804 | 4/1992 | Humphries et al. . | |
| 5,112,134 | 5/1992 | Chow et al. . | |
| 5,160,702 | 11/1992 | Kopf-Sill et al. . | |
| 5,164,319 | 11/1992 | Hafeman et al. . | |
| 5,169,601 | 12/1992 | Ohta et al. . | |
| 5,192,510 | 3/1993 | Zoha et al. . | |
| 5,206,568 | 4/1993 | Bjornson et al. . | |
| 5,208,161 | 5/1993 | Saunders et al. . | |
| 5,208,651 | 5/1993 | Buican . | |
| 5,225,164 | 7/1993 | Astle . | |
| 5,257,202 | 10/1993 | Feddersen et al. . | |
| 5,270,788 | 12/1993 | Cercek et al. . | |
| 5,273,718 | 12/1993 | Sköld et al. . | |
| 5,275,951 | 1/1994 | Chow et al. . | |
| 5,278,048 | 1/1994 | Parce et al. . | |
| 5,315,015 | 5/1994 | Hui et al. . | |
| 5,317,485 | 5/1994 | Merjanian . | |
| 5,319,436 | 6/1994 | Manns et al. . | |
| 5,323,008 | 6/1994 | Studholme et al. . | |
| 5,323,010 | 6/1994 | Gratton et al. . | |
| 5,340,716 | 8/1994 | Ullman et al. . | |
| 5,340,747 | 8/1994 | Eden . | |
| 5,353,112 | 10/1994 | Smith . | |
| 5,355,215 | 10/1994 | Schroeder et al. . | |
| 5,361,626 | 11/1994 | Colligan et al. . | |
| 5,384,093 | 1/1995 | Ootani et al. . | |
| 5,395,503 | 3/1995 | Parce et al. . | |
| 5,401,465 | 3/1995 | Smethers et al. . | |
| 5,418,371 | 5/1995 | Aslund et al. . | |
| 5,420,408 | 5/1995 | Weyrauch et al. . | |
| 5,436,718 | 7/1995 | Fernandes et al. . | |
| 5,445,935 | 8/1995 | Royer . | |
| 5,449,921 | 9/1995 | Baba . | |
| 5,457,527 | 10/1995 | Manns et al. . | |
| 5,459,300 | 10/1995 | Kasman . | |
| 5,480,804 | 1/1996 | Niwa et al. . | |
| 5,485,530 | 1/1996 | Lakowicz et al. . | |
| 5,487,872 | 1/1996 | Hafeman et al. . | |
| 5,491,343 | 2/1996 | Brooker . | |
| 5,496,697 | 3/1996 | Parce et al. . | |
| 5,500,188 | 3/1996 | Hafeman et al. . | |
| 5,512,492 | 4/1996 | Herron et al. . | |
| 5,528,046 | 6/1996 | Ishikawa . | |
| 5,529,752 | 6/1996 | Pontis et al. . | |
| 5,537,343 | 7/1996 | Kikinis et al. . | |
| 5,542,012 | 7/1996 | Fernandes et al. . | |
| 5,557,398 | 9/1996 | Wechsler et al. . | |
| 5,561,068 | 10/1996 | Rounbehler et al. . | |
| 5,567,302 | 10/1996 | Song et al. . | |
| 5,589,136 | 12/1996 | Northrup et al. . | |
| 5,589,350 | 12/1996 | Bochner . | |
| 5,589,351 | 12/1996 | Harootunian . | |
| 5,592,289 | 1/1997 | Norris . | |
| 5,593,867 | 1/1997 | Walker et al. . | |
| 5,595,710 | 1/1997 | Van Dusen et al. . | |
| 5,599,500 | 2/1997 | Jones . | |
| 5,604,130 | 2/1997 | Warner et al. . | |
| 5,620,894 | 4/1997 | Barger et al. . | |
| 5,626,134 | 5/1997 | Zuckerman . | |
| 5,631,734 | 5/1997 | Stern et al. . | |
| 5,633,724 | 5/1997 | King et al. . | |
| 5,635,402 | 6/1997 | Alfano et al. . | |
| 5,641,633 | 6/1997 | Linn et al. . | |
| 5,650,832 | * 7/1997 | Poradish et al. | 348/743 |
| 5,663,545 | 9/1997 | Marquiss . | |
| 5,676,943 | 10/1997 | Baetge et al. . | |
| 5,679,310 | 10/1997 | Manns . | |
| 5,736,410 | 4/1998 | Zarling et al. . | |
| 5,766,875 | 6/1998 | Hafeman et al. . | |
| 5,780,857 | 7/1998 | Harju et al. . | |
| 5,825,617 | 10/1998 | Kochis et al. . | |
| 5,842,582 | 12/1998 | DeStefano, Jr. . | |

| | | |
|---|---|---|
| 5,905,571 | 5/1999 | Butler et al. . |
| 5,959,738 | 9/1999 | Hafeman et al. . |

OTHER PUBLICATIONS

Jeffrey Sipior et al., "A Lifetime–Based Optical $CO_2$ Gas Sensor with Blue or Red Excitation and Stokes or Anti–Stokes Detection," *Analytical Biochemistry*, 227, 309–318 (1995).

*Fundamentals of Light Microscopy*, Spencer, Cambridge University Press, 1982.

*Basic Fluorescence Microscopy*, Taylor et al., *Methods in Cell Biology*, vol. 29, pp. 207–237, 1989.

*Quantitative Fluorescence Microscopy Using Photomultiplier Tubes and Imaging Detectors*, Wampler et al., *Methods in Cell Biology*, vol. 29, pp. 239–267, 1989.

*Three–Dimensional Confocal Fluorescence Microscopy*, Brakenhoff et al., *Methods in Cell Biology*, vol. 30, pp. 379–389, 1989.

*Laser Scanning Confocal Microscopy of Living Cells*, Lemasters et al., *Optical Microscopy: Emerging Methods and Applications*, pp. 339–345, 1993.

*Time–Resolved Fluorescence Lifetime Imaging*, vandeVen et al., *Optical Microscopy: Emerging Methods and Applications*, pp. 373–389, 1993.

Tecan SPECTRAfluor—A Step Forward in Microplate Fluorometry, internet description pages, printed from internet on Jun. 17, 1998.

Wallac Time–Resolved Fluorometry—The Key to Improved Assay Sensitivity, internet description pages, printed from internet on Jul. 7, 1998.

Wallac 1234 DELFIA Fluorometer, internet description page, printed from internet on Jul. 7, 1998.

Wallac 1420 VICTOR Multilabel Counter, internet description pages, printed from internet on Jul. 7, 1998.

Wallac 1420 VICTOR $^2$ Multilabel Counter, internet description pages, printed from internet on Jul. 7, 1998.

Wallac 1442 ARTHUR Multi–Wavelength Fluoroimager, internet description page, printed from internet on Jul. 7, 1998.

Wallac Labelling Reagents for Time–Resolved Fluorometry, internet description page, printed fron internet on Jul. 7, 1998.

* cited by examiner

OPTICAL FILTER HOLDER ASSEMBLY

CROSS-REFERENCES TO RELATED APPLICATIONS

This application is a related application of the following patent applications, each of which is incorporated herein by reference: U.S. patent application Ser. No. 09/062,472, filed Apr. 17, 1998 U.S. Pat. No. 6,071,768; and PCT patent application Ser. No. PCT/0398/14575, filed Jul. 15, 1998, This application is based upon and claims benefit under 35 U.S.C. §119 of the following U.S. Provisional Patent Applications, each of which is incorporated herein by reference: Ser. No. 60/052,876, filed Jul. 16, 1997; Ser. No. 60/059,639, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; and Ser. No. 60/089,848, filed Jun. 19, 1998.

This application incorporates by reference the following U.S. patent applications: Ser. No. 09/118,341 filed Jul. 16, 1998 now U.S. Pat. No. 6,025,985, and Ser. No. 09/118,310 filed Jul. 16, 1998, now U.S. Pat. No. 6,033,600.

FIELD OF THE INVENTION

The invention relates to optical filters. More particularly, the invention relates to devices for using optical filters in a filter holder that enable optical filters to be simply, conveniently, and flexibly interchanged.

BACKGROUND OF THE INVENTION

Optical systems typically include many components, which interact to generate, transmit, modify, and detect light. Light may be generated by light sources, transmitted by optical relay structures, and detected by detectors. Light may be modified by optical filters positioned in an optical path in one or both of the light source and detector ends of the instrument.

Optical filters modify the intensity, spectrum, polarization, and other properties of light. "Intensity filters" modify the intensity of light, where intensity is the amount of light per unit area per unit time. Intensity filters may absorb light, dissipating the absorbed energy as heat, or they may reflect or scatter light. "Spectral filters" modify the spectrum of light, where spectrum is the wavelength composition of light. Spectral filters may selectively transmit light of preselected wavelengths and selectively absorb, reflect, or scatter light of other wavelengths. A spectral filter may convert light of many colors into light of one or only a few colors. "Polarization filters" modify the polarization of light, where polarization is the direction of the electric field associated with light.

Different applications or conditions may require different optical filters. For this reason, filter holders have been developed that allow one of a plurality of optical filters to be selected and placed in an optical path. Examples include filter wheels and filter slides. Unfortunately, these filter holders have a number of shortcomings. In particular, the number of optical filters required even for a single application often exceeds the filter-holding capacity of a given filter holder. Therefore, it sometimes is necessary to replace the optical filters within a given filter holder.

Replacing optical filters may be difficult and time-consuming. If individual optical filters are affixed permanently to the filter holder, the entire filter holder may need to be replaced. If individual optical filters are affixed to removable filter cartridges within the filter holder, the filter holder still must be opened, individual filter cartridges removed and replaced, and the filter holder closed again. In known filter holders, filter cartridges must be replaced with the filter holder attached to an associated instrument. Working space may be minimal, and filter cartridges and other components may be dropped into the instrument, where they may cause damage and be difficult to retrieve.

Replacing optical filters within filter cartridges also may be difficult and time-consuming. Many or most optical filters are permanently affixed to any associated filter cartridge, and may not be replaced at all. Other optical filters may be removably affixed to an associated filter cartridge, but replaceable only with a limited selection or number of filters. Filter cartridges with removable optical filters may employ a retaining ring that fits into a groove on the inside of the filter cartridge to hold the optical filter. The groove establishes a predetermined position for the retaining ring, and may limit the thickness or number of replacement filters. Optical filters that are thicker than the provided space will not fit, and optical filters that are thinner than the provided space may require spacers. Filter cartridges with removable optical filters also may employ a threaded retention member that can be screwed into the filter cartridge until a point where it holds the optical filter. This approach may require extra tools and be time-consuming. This approach also may force the retaining ring into a plane that is slightly skewed relative to the filter, misaligning the optical filter.

SUMMARY OF THE INVENTION

The present invention addresses these and other shortcomings by providing filter cartridges and filter holders that enable optical filters to be simply, conveniently, and flexibly interchanged.

In one embodiment, the invention provides a device for holding an optical filter that includes a filter barrel having an inner wall and a stop structure, a removable annular friction member inside the filter barrel, and at least one optical filter sandwiched between the stop structure and the friction member. In this embodiment, the friction member is held in place relative to the inner wall by static friction, without any thread, groove, or adhesive. The filter barrel and friction member may take a variety of forms and may hold optical filters of various sizes and numbers. The friction member may hold the optical filter snugly in place during routine use, while also permitting easy removal when replacing optical filters.

In another embodiment, the invention provides a tool device for loading an optical filter into a holder. The device includes a funnel structure having a top end and a lower edge configured to rest on top of a filter holder. The funnel structure includes an inner diameter that enlarges gradually in a direction from the lower edge toward the top end. The device also may include a slug for applying pressure to a friction member when loading the optical filter.

In yet another embodiment, the invention provides an optical filter holder system that includes a holder having a plurality of apertures, and two sets of filter cartridges configured to fit in the apertures. The first set of filter cartridges includes an optical filter permanently fixed in the filter cartridge. The second set of filter cartridges includes a mechanism that permits easy replacement of different optical filters in the same filter cartridge. The filter holder may include a filter wheel, and the mechanism that permits easy replacement my include a filter barrel and friction member.

In yet another embodiment, the invention provides an optical filter wheel module including an optical filter wheel that is rotatable around a hub structure, and a wheel case having a static portion and a removable portion and at least one set of windows for transmitting light through the wheel case and through a selected optical filter contained in the optical filter wheel. The hub structure is built into the removable portion of the wheel case. The wheel case may be light tight and include more that one set of windows.

In yet another embodiment, the invention provides a device for holding an optical filter comprising a base having a hub structure, and an elongate filter cartridge having a filter end and a pivot end, the filter end configured to hold at least one optical filter, the pivot end configured turnably to attach to the hub structure, so that an optical filter can be turned between two positions about the hub structure.

The invention will be understood more readily after consideration of the drawings and the detailed description of the invention that follow.

DETAILED DESCRIPTION OF THE INVENTION

Figure 1:
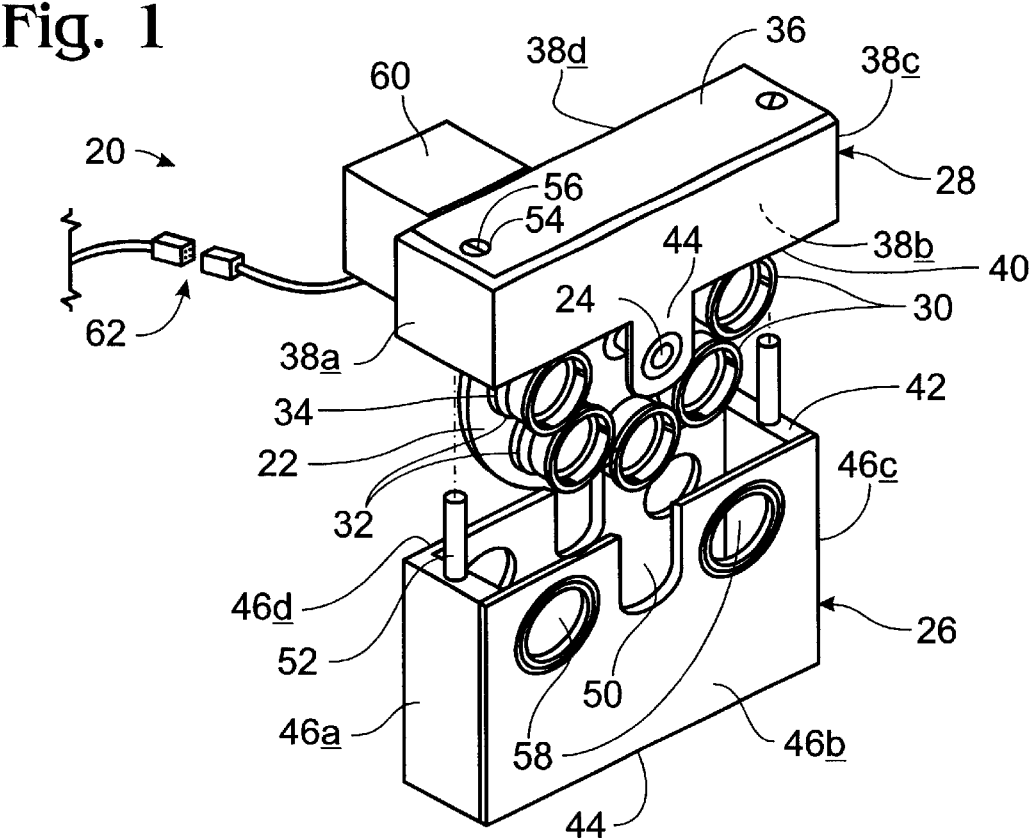
FIG. 1 is a partially exploded perspective view of an optical filter wheel assembly constructed in accordance with the invention.

FIG. 1 shows a partially exploded perspective view of an optical filter wheel assembly 20 constructed in accordance with the present invention. Optical filter wheel assembly 20 includes a filter wheel 22 that is rotatable about a hub structure 24, and a wheel case having a static base portion 26 and a removable lid portion 28. Hub structure 24 is built into removable lid portion 28.

Filter wheel 22 holds filter cartridges 30. Filter wheel 22 is substantially circular and includes a plurality of apertures 32 disposed symmetrically about its outer perimeter 34. Apertures 32 are used for mounting filter cartridges 30 and may hold the filter cartridges via friction, threads, or other means. Filter wheel 22 may have a variety of shapes, and apertures 32 may be disposed in a variety of configurations, although a symmetric embodiment is preferred for balance and ease of rotation about hub structure 24.

Removable lid portion 28 holds filter wheel 22. Removable lid portion 28 is substantially rectangular, with an enclosed top 36 and sides 38a–d and an open bottom 40 for receiving filter wheel 22. Opposed flanges 42 extend downward from one pair of opposed sides 38b,d of removable lid portion 28 to support hub structure 24. Filter wheel 22 is rotatably mounted through its center on hub structure 24.

Static base portion 26 holds removable lid portion 28 and filter wheel 22. Static base portion 26 is substantially rectangular, with an enclosed bottom 44 and sides 46a–d and an open top 48 for receiving filter wheel 22. Opposed slots 50 extend downward into one pair of opposed sides 46b,d of static base portion 26 to receive opposed flanges 42. Opposed posts 52 extend upward from the other pair of opposed sides 46a,c of static base portion 26 to be received by opposed holes 54 in opposed sides 38a,c of removable lid portion 28. Flanges 42 and slots 50, and posts 52 and holes 54, individually and collectively form a post-to-hole mating structure that aligns static base portion 26 and removable lid portion 28 when the two portions are mated together to form the wheel case. Captive screws 56 situated in holes 54 and accessible from top 36 may be threaded into posts 52 to hold together removable lid portion 28 and static base portion 26. Static base portion 26 further may be fixed to an instrument platform to form a portion of a light source module, detector module, or other optical assembly, among other applications.

The assembled wheel case is substantially light-tight, except for light that is transmitted through two sets of opposed windows 58 included in static base portion 26. Windows 58 are used for transmitting light through the wheel case and through a selected optical filter contained in a filter cartridge 30 in filter wheel 22. Windows 58 are located on opposite sides of hub structure 24, so that any given optical filter in filter wheel 22 can be rotated into alignment with either set of windows. In turn, light sources, detectors, and other optical components can be aligned with either or both sets of filters. Generally, the wheel case includes at least one set of windows, which may be located on the static portion, removable portion, or other portion of the wheel case.

Filter wheel 22 may be rotated by a drive motor 60, which is attached to removable lid portion 28 in optical filter wheel assembly 20. Drive motor 60 or other drive mechanisms also may be operatively connected to optical filter wheel assembly 20 at other points and in other manners.

FIG. 1 also shows a mechanism by which optical filter wheel assembly 20 may be disassembled and reassembled. Optical filter wheel assembly 20 is disassembled as follows. First, any associated instrument is powered down and unplugged. Second, any secondary housing enclosing optical filter wheel assembly 20 is removed. Third, drive motor 60 is unplugged at its inline connector 62. Fourth, captive screws 56 are loosened. Finally, removable lid portion 28 and filter wheel 22 are pulled out of static base portion 26.

Optical filter wheel assembly 20 may be reassembled as follows. First, filter cartridges 30 are checked to verify that they are properly seated in filter wheel 22, and filter wheel 22 is checked to verify that it rotates smoothly about hub structure 24 when moved by hand. Second, removable lid portion 28 and filter wheel 22 are inserted into static base portion 26, aligning flanges 42 with slots 50, and posts 52 with holes 54. Third, captive screws 56 are tightened. Fourth, drive motor 60 is plugged back in at inline connector 62. Fifth, any secondary housing is replaced. Finally, any associated instrument is plugged back in and powered up, if desired.

Figure 2:
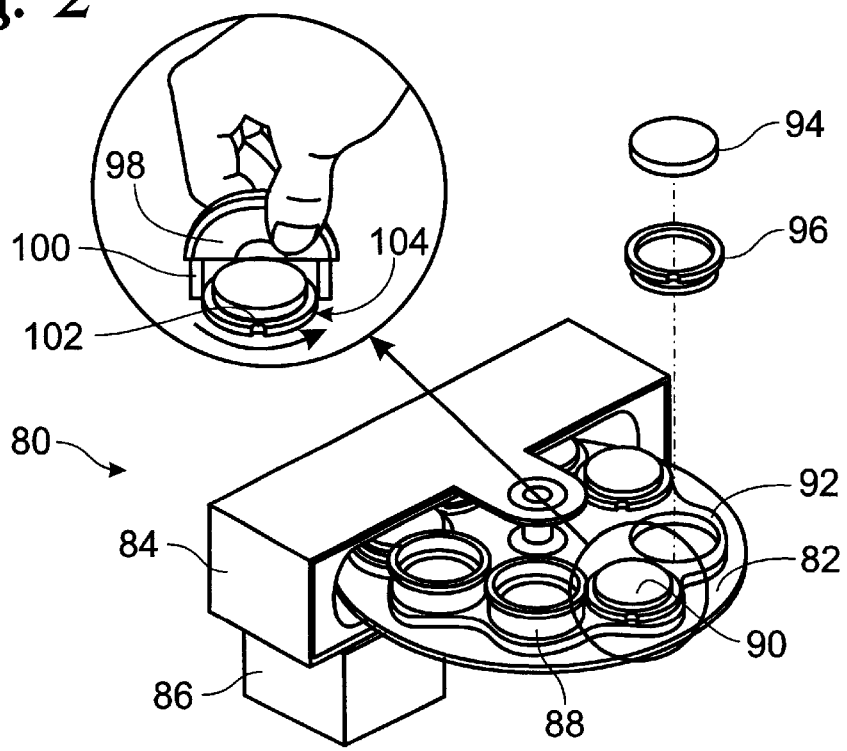
FIG. 2 is a partially exploded perspective view of a portion of an optical filter wheel assembly like that shown in FIG. 1, showing a mechanism by which short filter cartridges may be removed.

FIG. 2 shows a partially exploded perspective view of a removable portion 80 of an optical filter wheel assembly, including a filter wheel 82, removable lid portion 84, and drive motor 86. Filter wheel 82 includes a set of "short" filter cartridges 88 and a set of "tall" filter cartridges 90. Filter wheel 82 may hold a variety of filter cartridges, so long as the filter cartridges are configured to fit in apertures 92 in the filter wheel. Generally, opposed apertures in filter wheel 82 should contain matching filter cartridges or a suitable slug to balance the filter wheel and to prevent unfiltered radiation from reaching a detector.

FIG. 2 also shows a mechanism by which short filter cartridges 88 may be removed and replaced. Generally, short filter cartridges 88 include an optical filter 94 permanently affixed by suitable means, such as glue, to a short filter barrel 96 having a low profile. Optical filter 94 may include an intensity filter, a spectral filter, or a polarization filter, among others. Short filter cartridges 88 are removed from filter wheel 82 as follows. First, with the filter wheel removed as described above, the desired short filter cartridge is located by sight or by location. (Filter cartridge locations within the filter wheel may be marked on the filter wheel or elsewhere for reference.) Second, the short filter cartridge is removed by turning it counter-clockwise, which unscrews it. The short filter cartridge may be turned by hand or by a special tool, such as a spanner wrench 98 having prongs 100 that engage grooves 102 in the sides of the short filter cartridge 104. Finally, filter changes are noted on the filter wheel or elsewhere and in any associated instrument software. Short filter cartridges 88 may be replaced in filter wheel 82 by reversing the process, turning the short filter cartridge clockwise.

Figure 3:
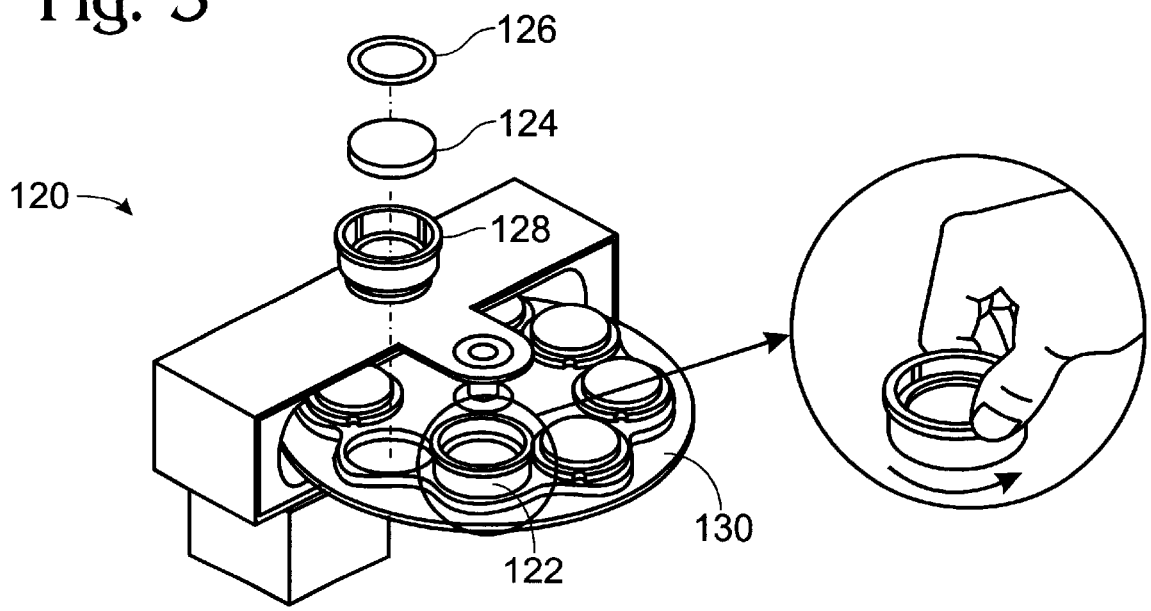
FIG. 3 is a partially exploded perspective view of the portion of the optical filter wheel assembly shown in FIG. 2, showing a mechanism by which tall filter cartridges may removed.

FIG. 3 shows a partially exploded perspective view of a removable portion 120 of an optical filter wheel assembly, as shown in FIG. 2. FIG. 3 also shows a mechanism by which tall filter cartridges 122 may be removed and replaced. Generally, tall filter cartridges 122 include an optical filter 124 affixed by a removable friction member 126 to a tall filter barrel 128. Optical filter 124 may include an intensity filter, a spectral filter, or a polarization filter, among others. Friction member 126 and tall filter barrel 128 may be substantially annular. Tall filter cartridges 122 may be removed from and replaced in filter wheel 130 much like short filter cartridges 88; however, tall filter cartridges 122 generally are turned by hand rather than by a tool.

Figure 4:
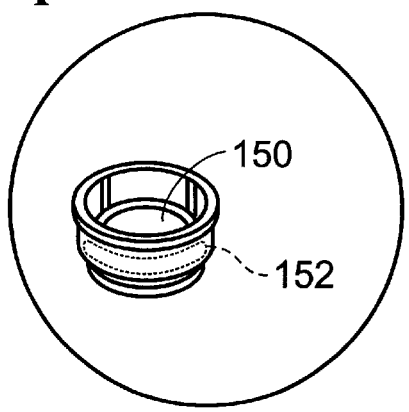
FIG. 4 is a perspective view showing a mechanism by which optical filters may be placed in a tall filter cartridge.
Figure 5:
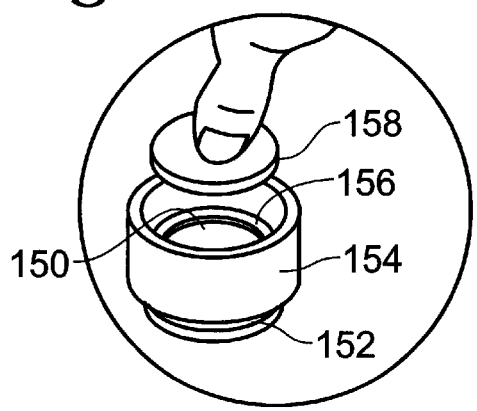
FIG. 5 is a perspective view showing a mechanism by which a friction member may be pressed into place using a funnel and slug.

FIGS. 4 and 5 show a perspective view of a mechanism by which optical filters may be replaced in the tall filter cartridges. First, as shown in FIG. 4, the optical filter 150 is placed in the tall filter barrel 152. Optical filter 150 should be oriented properly if one side is different than the other. Additional optical filters 150 can be placed in tall filter barrel 152, if desired. Second, as shown in FIG. 5, a funnel structure 154 is placed on top of tall filter barrel 152. Third, an annular friction member 156 is placed in funnel structure 154, followed by a slug 158. Slug 158 and optical filter 150 have approximately equivalent peripheral dimensions, including radii. Fourth, slug 158 is pushed down through funnel structure 154 to compress friction member 156, which should fit snugly against optical filter 150. Finally, slug 158 and funnel structure 154 are removed. The completed tall filter cartridge then can be installed in a filter wheel, as described above.

Optical filter 150 also may be replaced by other techniques. Generally, the tall filter cartridges incorporate a mechanism that permits easy replacement of different optical filters in the same cartridge, enhancing the flexibility of the tall cartridges.

Optical filter 150 may be removed from the tall filter cartridge as follows. First, a lint-free cloth is placed on a work surface. Second, the installed optical filter 150 (or slug 158) is pushed gently near its center with a gloved finger or thumb, which will cause the optical filter 150 and friction member 156 to drop out of tall filter barrel 152. Removed optical filter 150 should be stored so that it will not become dirty or scratched.

Figure 6:
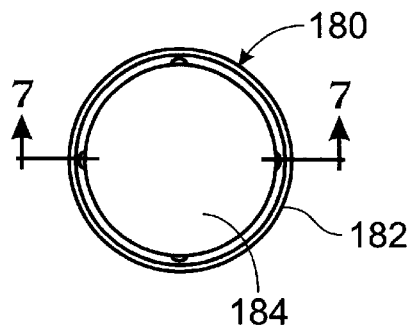
FIG. 6 is a top view of a short filter cartridge constructed in accordance with the invention.
Figure 7:
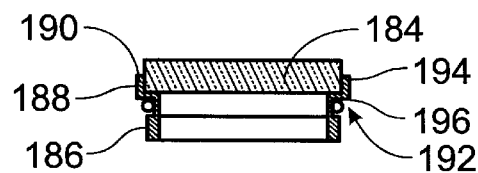
FIG. 7 is a cross-sectional view of the short filter cartridge, taken generally along the line 7—7 in FIG. 6.

FIGS. 6 and 7 show detailed views of a short filter cartridge 180, which includes a short filter barrel 182 and optical filter 184. Short filter barrel 182 is substantially annular, with a threaded lower portion 186 that screws into an aperture in a filter wheel, and a graspable upper portion 188 having a knurled rim 190 that may be turned by hand. Optical filter 184 is supported by upper portion 188, and mounts adjacent a stop structure 192 and inner wall 194 on short filter barrel 182, so that it is substantially centered relative to short filter barrel 182. Stop structure 192 includes an edge 196 oriented substantially perpendicular to a principal plane of optical filter 184 and to inner wall 194.

Figure 8:
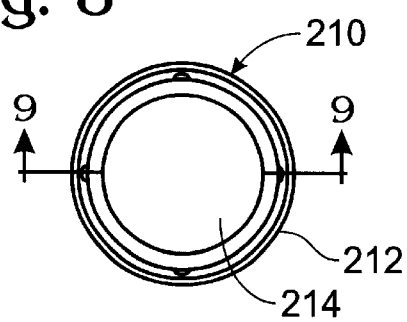
FIG. 8 is a top view of a tall filter cartridge constructed in accordance with the invention.
Figure 9:
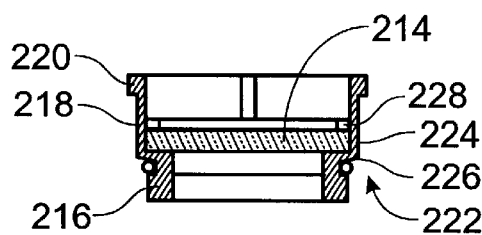
FIG. 9 is a cross-sectional view of the tall filter cartridge, take generally along the line 9—9 in FIG. 8.

FIGS. 8 and 9 show detailed views of a tall filter cartridge 210, which includes a tall filter barrel 212 and optical filter 214. Tall filter cartridge 210 resembles short filter cartridge 180 in many respects. Tall filter barrel 212 is substantially annular, with a threaded lower portion 216 that screws into an aperture in a filter wheel, and a graspable upper portion 218 having a knurled rim 220 that may be turned by hand. Optical filter 214 is supported by upper portion 218, and mounts adjacent a stop structure 222 and inner wall 224. Stop structure 222 includes an edge 226 oriented substantially perpendicular to a principal plane of optical filter 214 and to inner wall 224. Inner wall 224 may be substantially perpendicular to the optical filter, as here, or it may have a funnel portion that graduates in diameter in a direction toward the stop structure, among other configurations. Lower portion 186 of short filter barrel 182 is substantially identical to lower portion 216 of tall filter barrel 212. However, upper portion 188 of short filter barrel 182 is shorter than upper portion 218 of tall filter barrel 212, giving it a lower profile. In addition, optical filter 184 of short filter barrel 182 is permanently affixed to upper portion 188, whereas optical filter 214 of tall filter barrel 212 is removably sandwiched in upper portion 218 between stop structure 222 and a friction member 228. Friction member 228 holds optical filter 214 in place relative to inner wall 224 in tall filter cartridge 210 by static friction, without any thread, groove, or adhesive. For this reason, among others, optical filters of various numbers and sizes may be secured.

Friction member 228 may take a variety of forms, including a compressible ring having an uncompressed outer diameter greater than the inner diameter of inner wall 224. The compressible ring may exert a force on the inner wall that provides sufficient static friction to hold an optical filter snugly in place during routine use, while also permitting easy removal when replacing optical filters.

Figure 10:
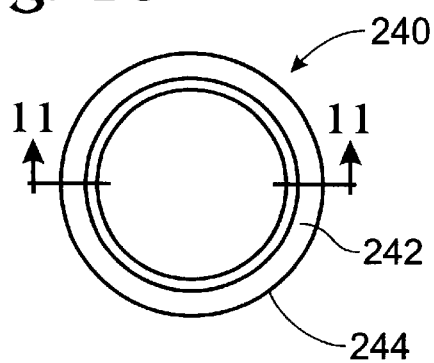
FIG. 10 is a top view of a funnel structure constructed in accordance with the invention.
Figure 11:
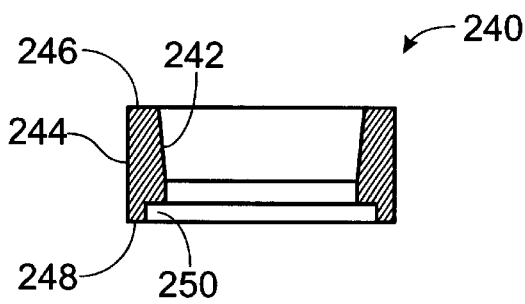
FIG. 11 is a cross-sectional view of the funnel structure, taken generally along the line 11—11 in FIG. 10.

FIGS. 10 and 11 show detailed views of a funnel structure 240, which is used for loading an optical filter into a tall filter cartridge or other holder as described above. Funnel structure 240 is substantially annular and includes inner and outer walls 242, 244 and a top end 246 and lower edge 248. Lower edge 248 includes a groove 250 adjacent inner wall 242 configured to rest on top of a filter cartridge or other holder. The inner diameter of funnel structure 240 measured between inner walls 242 enlarges gradually in a direction from lower edge 248 to top end 246.

Figure 12:
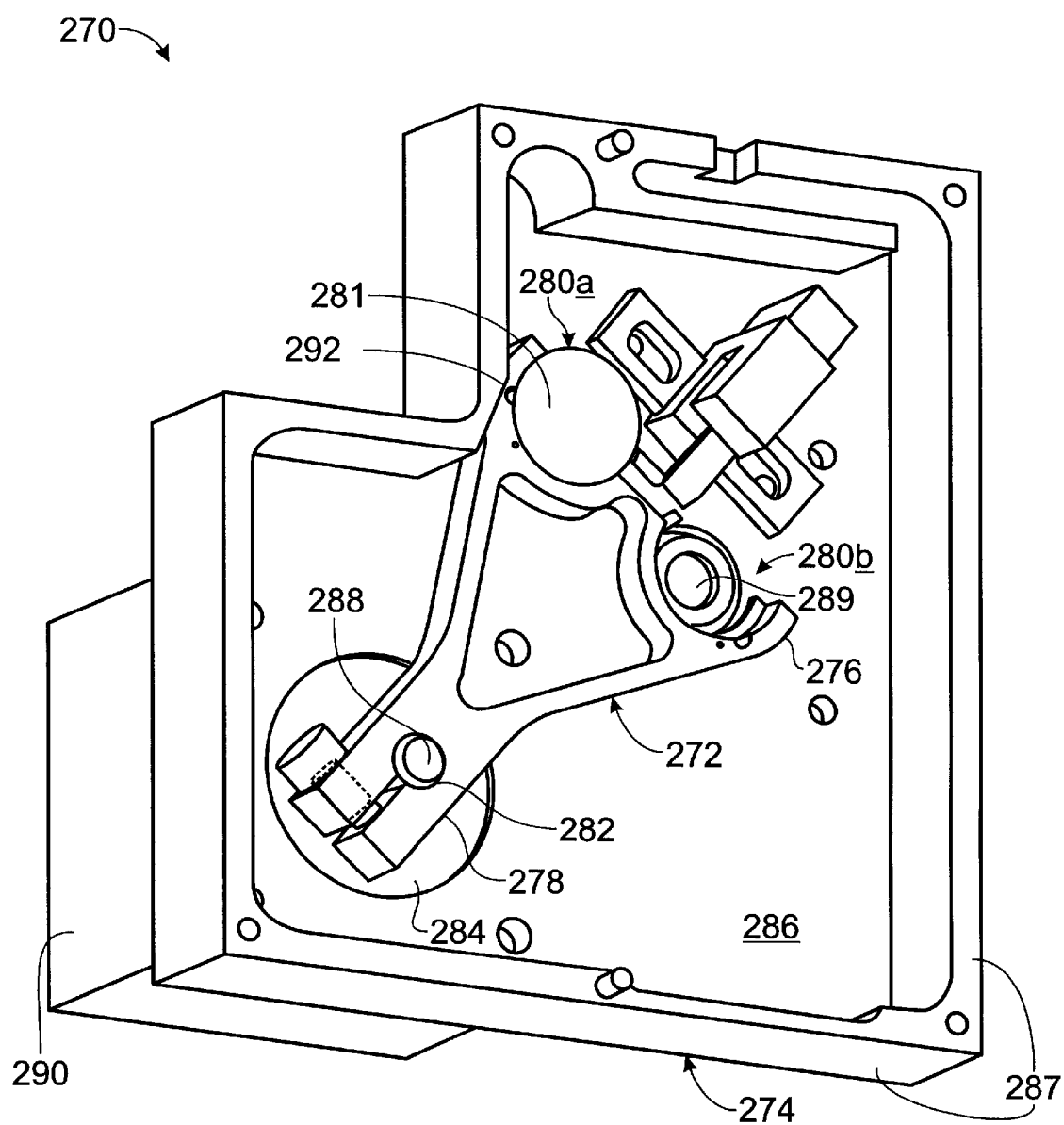
FIG. 12 is a partial perspective view of an alternative filter holder assembly constructed in accordance with the invention.

FIG. 12 shows a partial perspective view of an alternative filter holder assembly 270. Filter holder assembly 270 includes an elongate filter cartridge 272 and a base 274. Elongate filter cartridge 272 includes a filter end 276 and a pivot end 278. Filter end 278 is configured to hold optical filters, and includes two filter slots 280a,b in which optical filters 281 may be glued or otherwise attached. Generally, the filter end may hold one or more optical filters, using slots, apertures, short or tall filter cartridges, or other mechanisms. Filter slots may be left open to allow light to pass unfiltered, include filters to filter light, or include slugs or other opaque structures to block light. Pivot end 278 is configured turnably to attach to a hub structure, and includes an aperture 282 for receiving a drive axle or other pivot structure. Generally, the pivot end may attach through any means to any suitable drive mechanism. Elongate filter cartridge 278 is fan shaped, filter end 276 being wider than pivot end 272, although other shapes also are possible.

Base 274 generally supports elongate filter cartridge 272. Base 274 includes a hub structure 284 and major and walls 286, 287 that substantially surround elongate filter cartridge 272 on all but one side. Elongate filter cartridge 272 is turnably attached at its pivot end 278 to hub structure 284 through a drive axle 288, about which it may turn. Base 274 also includes a window 289 in major wall 286.

Elongate filter cartridge 272 may be used for moving an optical filter in and out of an optical path, much like a filter wheel or filter slide, by turning elongate filter cartridge 272 about hub structure 284. Because elongate filter cartridge 272 may move one or a few filters in and out of an optical path by turning through a limited angle, it may be configured to require less space than a filter wheel of comparable radius. A drive mechanism 290 may be controlled or base 274 may be configured to limit the angle through which elongate filter cartridge 272 may turn. For example, in filter holder assembly 270, a position 292 on minor wall 287 forms a stop structure that physically limits movement if drive mechanism 290 attempts to turn elongate filter cartridge 272 past the wall.

Figure 13:
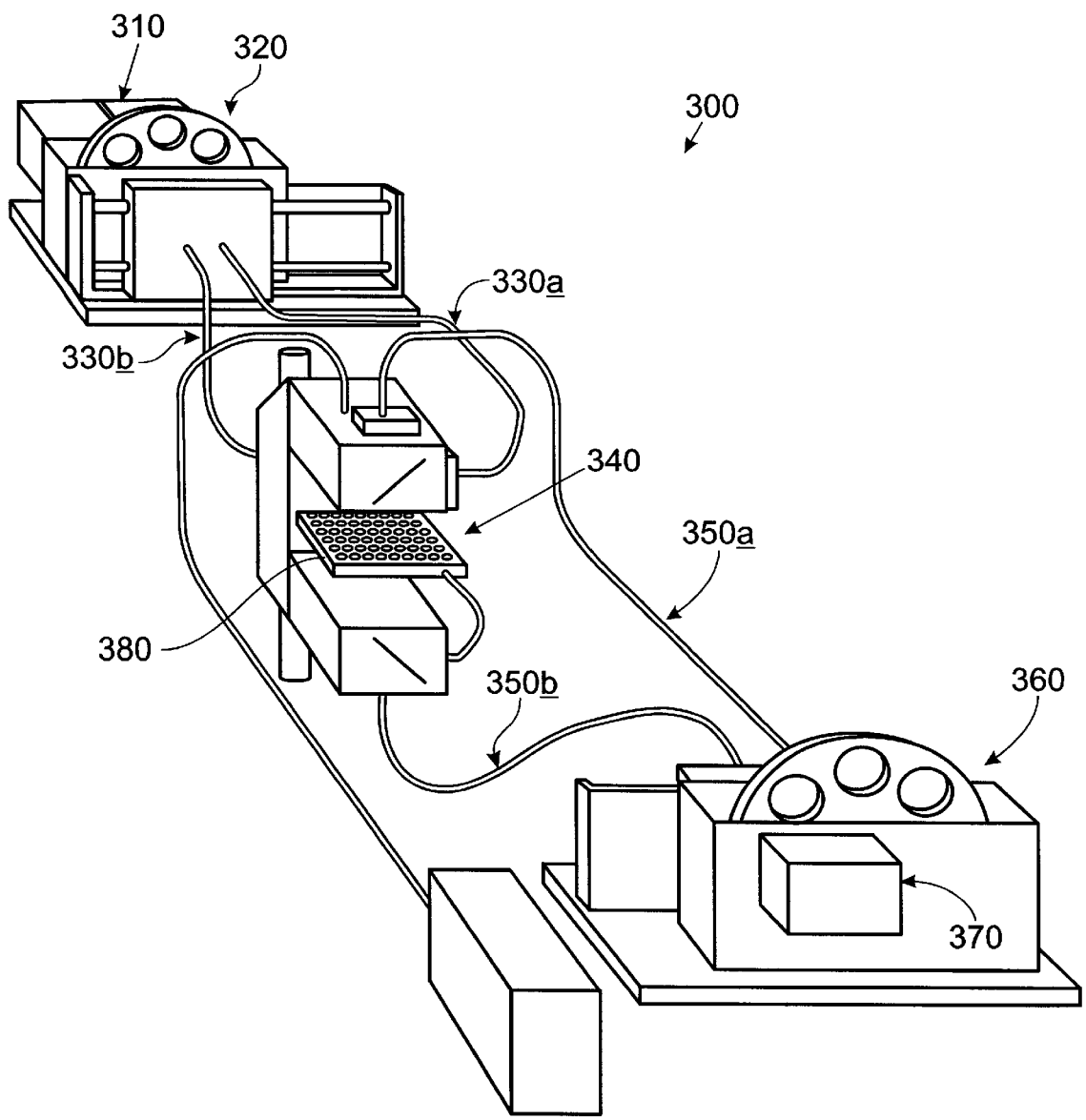
FIG. 13 is a schematic, partial perspective view of an exemplary light detection system incorporating optical filter wheel assemblies.

FIG. 13 is a partial perspective view of an exemplary light detection system 300 that incorporates optical filter wheel assemblies in accordance with the invention. The light detection system includes a light source 310, an excitation optical filter wheel assembly 320, an excitation optical relay structure 330a,b an examination site 10, an emission optical relay structure 350a,b, an emission optical filter wheel assembly 360, and a detector 370. These components may be used in photoluminescence and chemiluminescence applications. For example, in photoluminescence applications, excitation light is directed from light source 310 through excitation optical filter wheel assembly 320 to select its wavelength, through at least a portion of excitation optical relay structure 330a,b, and onto a sample positioned in a sample holder 380 at examination site 10. Emission light from the sample is directed through at least a portion of emission optical relay structure 350a,b, through emission optical filter wheel assembly 360 to select its wavelength, and onto detector 370.

Accordingly, while the invention has been disclosed in preferred forms, the specific embodiments thereof as disclosed and illustrated herein are not to be considered in a limiting sense, because numerous variations are possible and no single feature, function, or property of the preferred embodiments are essential. The invention is to be defined only by the scope of the issued claims.

We claim:

1. An optical filter wheel module comprising
   an optical filter wheel that is rotatable around a rotational axis, and
   a wheel case having a static portion and a removable portion, and at least one window for transmitting light through the wheel case and through a selected optical filter contained in the optical filter wheel, wherein the removable portion of the case carries the filter wheel, and is separable from the static portion of the case in a direction substantially perpendicular to the rotational axis so that the static portion of the case can remain fixed in relation to an optical axis while changing one or more filters in the filter wheel.

2. The module of claim 1, wherein the static portion has a pair of pins oriented generally perpendicular to the rotational axis, and the removable portion has a pair of holes for receiving the pins.

3. The module of claim 1, wherein the removable portion has a hub structure and the static portion has a cut-out for receiving the hub structure.

4. The module of claim 1, wherein static portion has two windows positioned on opposite sides of the rotational axis of the filter wheel, so that any given optical filter in the optical filter wheel can be rotated into alignment with either window.

5. The module of claim 1, wherein the filter wheel has multiple filter positions, the removable portion of the case being configured so that at least some of the filter positions are exposed when the removable portion is separated from the static portion.

6. The module of claim 1, wherein the wheel case is substantially light-tight, except for light that is transmitted through the window.

7. The module of claim 1, wherein the window is in the static portion of the wheel case.

8. The module of claim 1, wherein the window is in the removable portion of the wheel case.

9. The module of claim 1, wherein the static portion of the wheel case is fixed to an instrument platform.

10. The module of claim 1, further comprising a drive mechanism configured to rotate the optical filter wheel.

11. A light detection system comprising
    an optical relay structure for directing light along an optical path to or from an examination site,
    an optical filter wheel having plural filter holders radially positioned around a rotary axis, the rotary axis being substantially parallel to the optical path so that rotation of the filter wheel around the rotary axis permits different optical filters to be positioned in the optical path, and
    a filter wheel handling member that permits the filter wheel to be removed from its operable position in the light detection system in a direction substantially perpendicular to the optical path, wherein the filter wheel handling member forms part of a filter wheel case, the filter wheel case having a lower portion that remains fixed relative to the optical path so that the filter wheel can be properly positioned relative to the optical path by engaging the handling member with the lower portion of the case.

12. A light detection system comprising an optical relay structure for directing light along an optical path to or from an examination site,
   an optical filter wheel having plural filter holders radially positioned around a rotary axis, the rotary axis being substantially parallel to the optical path so that rotation of the filter wheel around the rotary axis permits different optical filters to be positioned in the optical path, and
   a filter wheel case having an upper portion and a lower portion, the upper portion of the case holding an axle for rotating the filter wheel, the upper and lower portions being separable from each other in a direction perpendicular to the optical path.

13. The system of claim 12 further comprising a pin-in-hole engagement mechanism that aligns the upper and lower portions of the filter wheel case.

14. A filter wheel station for a light detection instrument comprising a registration structure that remains fixed in relation to an optical path and a rotary axis, a filter wheel, a removable carrier member attached to the filter wheel, and
   a mating device for engaging the carrier member and the fixed registration structure in a direction substantially perpendicular to the optical path.

15. The station of claim 14, wherein the fixed registration structure and the carrier member form a substantial housing around the filter wheel.

16. The station of claim 15, wherein the housing has at least one window for permitting transmission of light along the optical path and through a selected filter.

17. The station of claim 14, wherein the mating device includes a pair of pins and a pair of holes for receiving the pins.

18. The station of claim 17, wherein the pins are formed in the registration device, and the holes are located in the carrier member.

* * * * *

UNITED STATES PATENT AND TRADEMARK OFFICE
CERTIFICATE OF CORRECTION

PATENT NO. : 6,313,960 B2
DATED : November 6, 2001
INVENTOR(S) : Samuel A. Marquiss et al.

It is certified that error appears in the above-identified patent and that said Letters Patent is hereby corrected as shown below:

Column 1,
Line 8, delete "6,071,768" and insert -- 6,071,748 -- therefore.
Line 9, delete "PCT/0398/14575" and insert -- PCT/US98/14575 -- therefor.
Line 21, delete "60,089,848" and insert -- 60/089,848 -- therefor.
Line 25, delete "6,033,600" and insert -- 6,033,100 -- therefor.

Signed and Sealed this

Twenty-fourth Day of September, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,313,960 B2
DATED : November 6, 2001
INVENTOR(S) : Samuel A. Marquiss et al.

It is certified that error appears in the above-identified patent and that said Letters Patent is hereby corrected as shown below:

<u>Column 1,</u>
Line 8, delete "6,071,768" and insert -- 6,071,748 -- therefore.
Line 9, delete "PCT/0398/14575" and insert -- PCT/US98/14575 -- therefor.
Line 21, delete "60,089,848" and insert -- 60/089,848 -- therefor.
Line 25, delete "6,033,600" and insert -- 6,033,100 -- therefor.

Signed and Sealed this

Fifteenth Day of October, 2002

*Attest:*

*Attesting Officer*

JAMES E. ROGAN
*Director of the United States Patent and Trademark Office*